US012606593B2

(12) United States Patent
Myers et al.

(10) Patent No.: US 12,606,593 B2
(45) Date of Patent: Apr. 21, 2026

(54) PROCESS FOR PRODUCING A MEMBRANE PROTEIN

(71) Applicant: AQUAPORIN A/S, Kongens Lyngby (DK)

(72) Inventors: Scott Treven Myers, Valby (DK); Torsten Høybye Bak Regueira, Værløse (DK); Lena Maria Than Ellingsgaard, Bjæverskov (DK); Simon Lyngaa Krabbe, Copenhagen (DK)

(73) Assignee: E. & J. Gallo Winery, Modesto, CA (US)

( * ) Notice: Subject to any disclaimer, the term of this patent is extended or adjusted under 35 U.S.C. 154(b) by 933 days.

(21) Appl. No.: 17/044,910

(22) PCT Filed: Apr. 5, 2019

(86) PCT No.: PCT/EP2019/058609
§ 371 (c)(1),
(2) Date: Oct. 2, 2020

(87) PCT Pub. No.: WO2019/193139
PCT Pub. Date: Oct. 10, 2019

(65) Prior Publication Data
US 2021/0147477 A1 May 20, 2021

(30) Foreign Application Priority Data

Apr. 6, 2018 (DK) .............................. PA201870202

(51) Int. Cl.
| | |
|---|---|
| *C07K 1/34* | (2006.01) |
| *C07K 1/16* | (2006.01) |
| *C07K 1/36* | (2006.01) |
| *C07K 14/705* | (2006.01) |

(52) U.S. Cl.
CPC ................ *C07K 1/34* (2013.01); *C07K 1/165* (2013.01); *C07K 1/36* (2013.01); *C07K 14/705* (2013.01)

(58) Field of Classification Search
None
See application file for complete search history.

(56) References Cited

U.S. PATENT DOCUMENTS

| | | | | |
|---|---|---|---|---|
| 5,468,847 A | * | 11/1995 | Heilmann ................ | C07K 1/34 530/416 |
| 2008/0207487 A1 | * | 8/2008 | DeFrees .................... | A61P 7/06 435/456 |
| 2013/0338344 A1 | * | 12/2013 | Ramasubramanyan ..................... | C12P 21/00 530/416 |
| 2021/0147477 A1 | | 5/2021 | Myers et al. | |

FOREIGN PATENT DOCUMENTS

| | | | |
|---|---|---|---|
| EP | 3774842 | A1 | 2/2021 |
| WO | 2010146365 | A1 | 12/2010 |
| WO | 2013043118 | A1 | 3/2013 |
| WO | 2014108827 | A1 | 7/2014 |
| WO | 2017137361 | A1 | 8/2017 |
| WO | 2019193139 | A1 | 10/2019 |

OTHER PUBLICATIONS

Borgnia et al., "Functional Reconstitution and Characterization of AqpZ, the *E. coli* Water Channel Protein", J. Mol. Biol., 291, 1169-1179, 1999, 11 total pages. (Year: 1999).*
Hang et al., "High-level production of aquaporin Z in *Escherichia coli* using maltose-binding protein/polyhistidine dual-affinity tag fusion system", Process Biochemistry, vol. 51, Issue 5, 599-606, 2016. (Year: 2016).*
Gomez et al., ("Gomez", "Flocculation of CHO cells for primary separation of recombinant glycoproteins: Effect on glycosylation profiles", Biochemical Engineering Journal, 132, 244-254, 2018. (Year: 2018).*
Japan Patent Office, Notification of Reason for Refusal, Application No. 2020554416, Mailed Oct. 25, 2022, 6 pages, English Translation 6 pages.
Intellectual Property Office of Singapore, Written Opinion, Application No. 11202009521Y, Dated Mar. 23, 2022, 7 pages.
European Patent Office, Communication pursuant to Article 94(3) EPC, Application No. 19716391.8, mailed Jun. 6, 2023, 5 pages.
Intellectual Property India, Examination report under sections 12 & 13 of the Patents Act, 1970 and the Patents Rules, 2003, Application No. 202027047498, Dated Jan. 16, 2023, 7 pages.
Borgnia M J et al: "Functional reconstitution and characterization of AqpZ, the *E. coli* water channel protein" Journal of Molecular Bio, Academic Press, United Kingdom, vol. 291, No. 5, XP004461916, ISSN: 002-2836, DOI: 10.1006/JMBI.1999.3032, Sep. 3, 1999, pp. 1171, 1177, 12 pages.
Hang et al: "High-level productions of aquaporin Z in*Escherichia coli* using maltose-binding protein/polyhistidine dual-affinity tag fusion system" Process Biochemistry, vol. 51, No. 5, XP029499319, ISSN: 1359-5113, DOI: 10.1016/J.PROCBIO.2016.02.002, Feb. 17, 2016, p. 601, 8 pages.

(Continued)

*Primary Examiner* — Jonathan M Peo
(74) *Attorney, Agent, or Firm* — Ziegler IP Law Group, LLC.

(57) ABSTRACT

A process for the production of a membrane protein is provided. The process including the steps of: expressing a membrane protein in a host organism present in an aqueous medium, liberating the membrane protein from the host organism, adding a detergent solution to solubilize the membrane protein, recovering a liquid fraction of the solubilized membrane protein, subjecting the liquid fraction to chromatography to bind or retain the membrane protein on a stationary phase, and eluting the stationary phase with an elution buffer to produce the membrane protein. The process can produce relatively large amounts of membrane proteins in an efficient way without compromising the quality of the end product.

17 Claims, No Drawings

(56)                    References Cited

OTHER PUBLICATIONS

Jesper et al: "Interaction between sodium dodecyl sulfate and membrane reconstituted aquaporins: A comparative study of spinach SoPIP1; 1 and *E. coli* AqpZ" Biochimica Et Biophysica Acta (BBA)—Biomembranes, Elsevier, Amsterdam, NL, vol. 1808, No. 10, XP028265621, ISSN: 0005-2736, DOI: 10.1016/J.BBAMEM. 2011.05.021, May 31, 2011, pp. 2600-2607, 8 pages.
Patent Cooperation Treaty, Notification of Transmittal of the International Preliminary Report on Patentability, Application No. PCT/ EP2019/058609, Mailed Jun. 5, 2020, 8 Pages.
Salt D E et al: "Selective flocculation of cellular contaminants from soluble proteins using polyethyleneimine: A study of several organisms and polymer molecular weights", Enzyme and Microbial Technology, vol. 17, No. 2, XP002722679, ISSN: 0141-0229, DOI: 10.1016/0141-0229(94)00043-Q, pp. 107-113, Feb. 1, 1995, 7 pages.
Wang et al: "One-Step extraction of functional recombinant aquaporin Z from inclusion bodies with optimal detergent", Protein Expression and Purification., vol. 115, XP055597375, ISSN: 1046-5928, DOI: 10.1016/j.pep.2015.08.014, Nov. 1, 2015, 7 pages.
Gomez et al: "Flocculation of CHO cells for primary separation of recombinant glycoproteins: Effect on glycosylation profiles" Biochemical Engineering Journal, vol. 132, XP055597470, ISSN: 1369-703X, DOI: 10.1016/j.bej.2018.01.027, pp. 244-254, Apr. 1, 2018, 11 Pages.
Canadian Intellectual Property Office, Examination Search Report, Application No. 3,095,674, Dated Oct. 20, 2023, 4 pages.
Federal Insitute of Industiral Property, Official Action, Application No. 2020136185, Dated Nov. 16, 2023, 5 pages.
State of Israel Ministry of Justice, Notice of Deficiencies, Application No. 277565, mailed Mar. 13, 2024, 3 pages, English Translation 3 pages.
Arun K. Mohanty et al, "Membrane protein expression and production: effects of polyhistidine tag length and position", Protein Expression and Purification 2004, vol. 33, p. 311-325, Issue 2, doi:10.1016/j.pep.2003.10.010, 16 pages.
Federal Service for Intellectual Property, Request Substantive Examination, Application No. 2020136185/04(066742), Mailed Aug. 16, 2022, 3 pages.
Federal Service for Intellectual Property, Search Report, PCT/ EP2019/058609, Date of completion Aug. 16, 2022, 2 pages.
The State Intellectual Property Office of People's Republic of China, The First Office Action. Application No. 201980023803.X, mailed Oct. 11, 2023, 10 pages, English Translation, 4 pages.
Korean Patent Office, Office Action pertaining to 10-2020-7031915, Dated May 20, 2024, 10 Pages English Translation, 12 Pages.
The State Intellectual Property Office of People's Republic of China, Second Office Action, Application No. 201980023803.X, Mailed Aug. 4, 2024, 3 pages.
Intellectual Property Office of Singapore, Written Opinion, Application No. 11202009521Y, Mailed Jan. 23, 2025, 6 pages.
Sanders et al, "Purifying His6-10-Tagged Membrane Proteins From *E. coli* and Making NMR Samples" Mar. 2017, 14 pages.
Japan Patent Office, Notice of Reasons for Refusal, Japanese Patent Application No. 2023-171068, Dated Oct. 15, 2024, 3 Pages.
Australian Government IP Australia, Examination report No. 1 for standard patent application, Application No. 2019249933, mailed Jan. 17, 2025, 4 pages.
Korean Intellectual Property Office, Notice of Final Rejection, Application No. 10-2020-7031915, mailed Jan. 3, 2025, 4 pages, English Translation 4 pages.
The State Intellectual Property Office of People's Republic of China, The Third Office Action, Application No. 201980023803.X, mailed Jan. 1, 2025, 6 pages, English Translation 8 pages.

* cited by examiner

1

PROCESS FOR PRODUCING A MEMBRANE PROTEIN

CROSS-REFERENCE TO RELATED APPLICATIONS

This application is a national phase of International Application No. PCT/EP2019/058609 filed Apr. 5, 2019 (published as WO 2019/193139), which claims priority to Denmark Application No. PA201870202 filed Apr. 6, 2018. The entirety for each of which is incorporated herein by reference.

TECHNICAL FIELD

The aspect of the disclosed embodiments relate to a process for producing a membrane protein. The process according to the disclosed embodiments is suitable for industrial application in which a large amount of membrane proteins is to be produced. Thus, the process aims at applying unit operations suitable for at least a pilot plant production. Notably, the aspects of the disclosed embodiments aim at avoiding an ultracentrifugation apparatus.

BACKGROUND

Approximately one-third of the genes in the human genome encode membrane proteins. Membrane proteins play a role in many important cellular activities including energy conversion, cell signaling, cell-cell interactions, cell adhesion, cell migration, protein trafficking, viral fusion, neural synaptic activities and ion and metabolite transport. Membrane proteins are embedded in the lipid bilayer of the cell membrane and are comprised of both hydrophobic and hydrophilic moieties.

Recently, membrane proteins have been successfully integrated into a thin film composite layer grafted onto a porous structural support layer. Furthermore, membrane proteins represent important pharmaceutical targets and interesting subjects of study with respect to cellular biology and protein biochemistry. A need therefore exists for pilot plant or large-scale production of membrane proteins.

WO2017137361 (A1) discloses self-assembled nanostructures formed between transmembrane proteins, such as aquaporin water channels (AQPs), and polyalkyleneimines (PAI). The self-assembled nanostructures are subsequently incorporated into thin film composite (TFC) membranes grafted onto a porous support membrane. The porous support membrane may be a hollow fiber, a flat sheet, a spiral wound membrane etc. for reverse osmosis or forward osmosis.

WO2013/043118 discloses thin film composite (TFC) membranes in which aquaporin water channels (AQPs) are incorporated in the active layer of the membrane. In addition, it discloses a method of producing thin film composite membranes and their uses in filtration processes, such as nanofiltration and osmotic filtration processes. The TFC membranes comprise lipid-AQP/copolymer-AQP vesicles that are incorporated in the TFC active layer. WO2010/146365 describes preparation of TFC-aquaporin-Z (AqpZ) filtration membranes that use an amphiphile triblock copolymer as a vesicle forming substance for incorporating immobilised AQPs.

WO2014/108827 discloses a hollow fiber (HF) module having fibers modified with a thin film composite (TFC) layer comprising aquaporin water channels in which the aquaporin water channels are incorporated in vesicles before incorporation into the TFC layer.

Industrial methods for isolating high amounts of membrane proteins from cells are generally not available for the person skilled in the art. In the prior art focus has been on the production of relatively small amounts of membrane proteins for research purposes. Therefore, a relatively cumbersome and labor-intensive production method has been tolerated. However, with the recent higher demands for membrane proteins in industrial membranes for reverse osmosis and forward osmosis a need for a more efficient production method has become clear. The object of the present disclosure is to provide a process for production of membrane proteins, where the process can produce relatively large amounts of membrane proteins in an efficient way without compromising the quality of the end product.

SUMMARY OF THE DISCLOSED EMBODIMENTS

The aspects of the disclosed embodiments relate to a process for producing a membrane protein, comprising the steps of:

a. Expressing a membrane protein in a host organism present in an aqueous medium,
  b. Liberating the membrane protein from the host organism,
  c. Adding a detergent solution to solubilize the membrane protein,
  d. Recovering a liquid fraction of the solubilized membrane protein as the supernatant by centrifugation,
  e. Subjecting the liquid fraction to chromatography to bind or retain the membrane protein on a stationary phase, and
  f. Eluting the stationary phase with an elution buffer to produce the membrane protein
  wherein the centrifugation in step d is performed at 500 g to 30,000 g.

The present process has the advantage of being able to handle a large amount of aqueous medium containing the host organism. Thus, the process is capable of handling amounts of 50 L or more, such as 100 L or more applying unit operations suitable for pilot plant or full-scale production. Furthermore, the process is scalable and may easily be adapted to high amounts of aqueous medium containing the host organism.

It has surprisingly been found by the inventors that the membrane proteins expressed by the host organism become solubilized to a higher extent than other proteins, when a detergent solution is added. It is estimated that at least around 60% of the proteins in the vesicles formed by the detergent solution are the membrane protein of interest. Furthermore, the vesicles formed of the detergent has been observed of a size which is larger than usual, such as around 0.5 um, suggesting that the membrane protein forms a more stable super form with the detergent than the phosphor lipids used by nature.

The aqueous medium containing the host organism may be used directly in the process. However, to obtain a cleaner product and to avoid handling of excess amounts of aqueous medium, generally the aqueous medium comprising the host organism of step a is filtered prior to the liberation of the membrane protein according to step b.

Generally, the aqueous medium comprising the host organism is up concentrated by filtering through a filter having pores small enough to allow cell debris and medium to pass, whereas the cells are retained. In a suitable embodiment, the aqueous medium comprising the host organism of step a is filtered through a microfiltration membrane having a pore diameter of 0.5 micrometer or less. Preferably, the pore diameter is 0.1 µm or less.

After the filtration step, suitably performed by microfiltration, the host organism may be isolated from the remainder of the aqueous medium. While several possible separation processes are possible it is generally preferred that the host organism is isolated after the filtration by centrifugation of the aqueous medium comprising the host organism. The centrifugation process is usually performed at a g-force which within a suitable time period forms a pellet. Therefore, the centrifugation is usually performed at 500 g or more, such as 1000 g or more, and preferably 2000 g and more. The density of the pellet should not be too high to prevent difficulties in the later steps. Therefore, the centrifugation is usually not performed above 30,000 g, such as not above 20,000 g, suitably not above 15,000 g and preferably not above 8,000 g.

The cells are harvested as the pellet and the supernatant may be discarded. It is preferred that the isolated host organism is washed with an isotonic saline solution to dissolve contaminating salts and subsequently centrifuged as described above to isolate the washed host organism. The spent washing solution appearing in the supernatant may be discarded.

The pellet containing the washed cells may be stored by freezing at −20° C. or used directly in the next step. Suitably, a dilution buffer is added prior to step b. The dilution buffer may contain protease inhibitors to prevent degradation of the membrane protein, pH regulating substances like TRIS and phosphate for maintaining a pH value within a desired range, and/or ion scavengers, such as EDTA.

The membrane protein may be liberated from the host organism in a number of ways, preferably by chemical or mechanical lysis of the cells. When chemical lysis of the cells is performed suitably an aqueous lysis solution is added to liberate the membrane protein from the host organism. In a preferred aspect of the disclosed embodiments, the aqueous lysis buffer is a detergent solution, which simultaneously solubilizes the membrane protein.

For the lysis of the cells and the solubilization of the membrane protein to take place, generally, the host cells are allowed to be subjected to the action of the detergent during agitation. Generally, the host cells are allowed to react with the detergent for at least one hour, such as 2 hours, and preferably at least 6 hours.

When mechanical lysis of the cells is used generally the liberation of the membrane protein from the host cells is performed by a homogenizer. It is suitable to use a homogenizer of the same type used in dairy industry for homogenization of milk. A suitable example includes the Stansted 7575 homogenizer. After treatment in the homogenizer the cells break open, liberating the membrane protein.

After the liberation of the membrane protein a cationic flocculant may be added. The cationic flocculant is believed to interact with inter alia negatively charged cell debris, thereby forming flocs. In a preferred aspect of the disclosed embodiments, the cationic flocculant is a polyamine compound, such as Superfloc C581.

The formation of flocs usually does not occur instantly. It is therefore preferred that the cationic flocculant is allowed to react with the cell parts of the resuspension during gentle agitation to form flocs. Usually the cationic flocculant and the cell debris are allowed to interact between 10 minutes and 2 hours while stirring at room temperature.

When chemical lysis of the cells is used, the liquid fraction of step e is recovered as the supernatant from a centrifugation of the suspension containing the flocs. The membrane protein appears in the supernatant as the membrane protein is solubilized by the detergent solution.

When mechanical lysis of the cells is used, the liquid fraction of step e is recovered from a resuspension of a solid fraction, wherein the solid fraction is resuspended in a detergent solution for solubilizing the membrane protein. In an embodiment, the solid fraction is formed due to the fact that the cell fragments containing the membrane protein interacts with the flocculant and form flocs, which may be separated from the liquid by centrifugation. In another embodiment, it was surprisingly found that it was possible to harvest the membrane protein in the pellet when a mechanical lysis of the cells was used, without the use of a flocculant. The pellet obtained by the centrifugation may be resuspended in a detergent solution for solubilizing the membrane protein. In this step, the liquid fraction of step e is harvested as the supernatant by centrifugation.

The centrifugation process is usually performed at a g-force which within a suitable time forms a pellet. Therefore, the centrifugation is usually performed at 500 g or more, such as 1000 g or more, and preferably 2000 g or more. The density of the pellet should not be too high to prevent difficulties in the later steps. Therefore, the centrifugation is usually not performed above 30,000 g, such as not above 20,000 g, suitably not above 10,000 g, and preferably not above 8,000 g. The application of a g-force below 30,000 g makes it possible to use a clarifier commonly used in dairies, such as spore-removing centrifuges from GEA, Tetra Pak, Alfa Laval, and SPX Flow Seital Separation Technology. The clarifiers useful in the present disclosure may also be referred to a Bactofuges by some manufactures. Thus, the aspects of the disclosed embodiments may omit the application of ultracentrifuges, which are only capable of batch centrifugation and treatment of small amounts.

Detergents used in the present disclosure include alkyl maltopyranosides, such as n-dodecyl-β-D-maltopyranoside (DDM), n-decyl-β-D-maltopyranoside (DM), or 5-cyclo-hexylpentyl β-D-maltoside (Cymal-5); alkyl glucopyranosides, such as n-octyl-β-D-glucopyranoside (OG); amine oxides, such as n-lauryl dimethylamine N-oxide (LDAO); phosphocholines such as n-Dodecylphosphocholine (FC-12), n-tetradecylphosphocholine (FC-14), or n-Hexadecylphosphocholine (FC-16); or polyoxyethylene glycols. In suitable embodiment of the present disclosure, the detergent is selected among from the group consisting of lauryl dimethylamine N-oxide (LDAO), octyl glucoside (OG), dodecyl maltoside (DDM) or combinations thereof. LDAO is a preferred detergent because large and stable vesicles are produced, suggesting that the detergent is capable of displacing the naturally occurring phospholipids.

The liquid fraction is subjected to a chromatography process in which the membrane protein is bonded to or retained by a stationary phase. The type of chromatography may be selected as affinity chromatography, ion exchange chromatography, size exclusion chromatography, displacement chromatography, liquid chromatography, high performance liquid chromatography, reversed-phase chromatography, hydrophobic interaction chromatography, etc. Usually, the chromatography process is preparatory chromatography, opposed to analytical chromatography, to form a purification of the membrane protein.

In a currently preferred embodiment, the chromatography method is selected as affinity chromatography, according to which a first part of an affinity pair is associated with the membrane protein and the second part of the affinity pair is associated with the stationary phase. Examples of a stationary phase include beads and column material. In a preferred embodiment of the present disclosure, the stationary phase associated with a second part of the affinity pair is present in a column. Usually, the parts of the affinity pairs are associated with covalent bindings to the membrane protein or the stationary phase. However, other types of association are also possible such as hybridization, affinity binding through antibody-antigen interaction, etc.

A number of affinity pairs applicable in the current disclosure is known to the person skilled in the art and include a biotin-streptavidin pair, an antibody-antigen pair, an antibody-hapten pair, an aptamer affinity pair, a capture protein pair, an Fc receptor-IgG pair, a metal-chelating lipid pair, a metal-chelating lipid-histidine (HIS)-tagged protein pair, or a combination thereof. In a currently preferred embodiment the affinity pair is a metal-chelating lipid-histidine (HIS)-tagged protein pair.

The metal is usually immobilized on the column material in a technology referred to as immobilized metal affinity chromatography (IMAC). The metal is usually selected as Cu(II) or Ni(II), preferably Ni(II). Using a Ni-NTA resin, His-tagged proteins can be automatically or manually be purified. A suitable stationary phase is "Capto Chelating" from GE healthcare or alternatively HisTrap Gel filtration material (Ni Sepharose 6 Fast Flow) from GE Healthcare.

The first part of the affinity pair being a histidine tag is usually attached to the C-terminal of the membrane protein. Whereas the histidine tag normally comprises 6 consecutive histidine amino acids it is preferred in the present disclosure that, the histidine tag comprises 8 or more histidine molecules. The high number of histidine amino acids in the histidine tag makes it possible to effectively separate the specific and the nonspecific binding proteins.

After the addition of the liquid fraction containing the membrane protein to the column the liquid is allowed by gravity or pressure to penetrate the resin. Suitably, the eluting buffer comprises imidazole. The imidazole has the ability to interact with the binding of the His tag to the metal ion immobilized on the resin. At a certain concentration of imidazole, the His tagged membrane protein will be liberated.

To separate the nonspecific binding membrane protein from the membrane protein of interest, generally, the column prior to the elution with the elution buffer, is washed with a washing buffer comprising 40% or less of the concentration of imidazole in the elution buffer. The concentration of imidazole in the elution buffer is generally in the range of 200 mM to 2000 mM imidazole. In preferred embodiments of the present disclosure, the concentration of imidazole in the elution buffer is 400 mM or more. To obtain a more effective elution of the His tagged membrane protein the concentration of imidazole in the buffers usually 600 mM or 800 mM or more.

For most applications, the His-tag generally has a negligible influence on protein structure, function, and immunogenicity. However, it may be desirable for certain applications to remove the His tag after it has served its function of binding the membrane molecule to the column. The His tag may be removed by introducing a cleavable link between the membrane protein and the His tag. Suitable cleavable links include pH sensitive linkers, disulfide linkers, protease sensitive linkers, and beta-glucuronide linkers.

Membrane proteins span in their natural environment the entire bilipid membrane, i.e. from the interior of the cell to the extracellular space. Many of the transmembrane proteins functions as gateways for specific substances, thereby allowing exchange of these substances between the interior of the cell and the extracellular liquid. A characteristic feature of transmembrane proteins is the presence of a hydrophobic area, which will ensure integration of the transmembrane protein into the membrane. The transmembrane protein furthermore has hydrophilic segments on both sides of the hollow fiber area, said hydrophilic segments being directed to the interior of the cell and the extracellular fluid, respectively.

While it is believed that any membrane protein can be produced in accordance with the present disclosure, it is generally desired to use the process to produce membrane proteins that transport ions (ion channels) and water (aquaporin water channels). Ion channels include chloride channels and metal ion transporters. Certain chloride channels in addition to the chloride ion also conducts $HCO_3^-$, $I^-$, $SCN^-$, and $NO_3^-$. The metal ion transporters include magnesium transporters, potassium ion channels, sodium ion channels, calcium channels, proton channels etc. In a certain embodiment of the present disclosure the membrane protein is outer membrane protein A (OmpA).

In a preferred embodiment of the present disclosure, the membrane protein is an aquaporin water channel. Aquaporin water channels facilitate the transport of water in or out of a cell. In an industrial membrane, the aquaporin water channels ensure the flow of water by osmosis, while other components in the solution are rejected. The membrane protein, such as an aquaporin water channel, may emanate from various sources including prokaryotic and eukaryotic organisms. A prokaryotic source for aquaporin includes *E. coli, Kyrpidia spormannii, Methanothermobacter* sp., *Novibacillus thermophilus, Saccharomyces cerevisiae*, and *Halomonas* sp. An eukaryotic source for aquaporin includes *Oryza sativa Japonica* (Japanese Rice), *Eucalyptus grandis, Solanum tuberosum* (Danish potato), and *Milnesium tardigradum* (water bear).

The nucleic sequence of the membrane protein from the source organism is generally codon optimized using Geneart's (Subsidiary of Thermo Fischer Scientific) service for improving expression in the host organism. The resulting gene is suitably synthesized with the addition of histidine encoding codons C-terminally, along with flanking restriction sites N-terminally and C-terminally. The synthetic gene fragment may be digested with the restriction enzyme and ligated into a vector fragment. The resulting ligation mixture is preferably transformed into an organism, such as *Escherichia coli* DH10B. The antibiotic resistant transformants are suitably selected on a medium with the antibiotic. Transformants were confirmed by sequencing of the genetic construct. Isolated vector DNA was subsequently transferred to the production host. The production host may be selected among a number of suitable prokaryotic or eukaryotic organisms, such as *Escherichia coli* and *Saccharomyces cerevisiae*.

The host organism is generally manipulated to express a native membrane protein in a higher amount than usual or to express non-native membrane protein. One way of expressing the membrane protein may be by transforming the host organism with a vector comprising DNA encoding the membrane protein, as discussed above. Another possibility for obtaining over-expression of the membrane protein would be by up-regulating the expression of a native membrane protein, e.g. by attenuating a repressor or insertion of a suitable promotor region. A further possibility for obtaining expression of a non-native protein would be to transfect a host organism with a virus or a bacteriophage containing a nucleic acid encoding the membrane protein.

EXAMPLES

Example 1

An *E. coli* BL21 strain is prepared comprising a vector producing aquaporin proteins linked to a His tag at the C-terminal. The His tag contains ten consecutive histidine molecules attached to the primary sequence of the aquaporin membrane protein.

The *E. coli* strain is nurtured in a standard medium to obtain a total fermentation broth of 150 L. The *E. coli* cells was harvested by filtering the fermentation broth through a microfiltration membrane having a pore diameter of 0.05 μm. The filtrate containing the *E. coli* cells is reduced to about 50 L and subsequently subjected to centrifugation at 5300 g for 20 minutes. Thus, the *E. coli* cells are up-concentrated by microfiltration and the remaining medium is subsequently removed as the supernatant by centrifugation.

The pellets obtained by the centrifugation are collected and added 1:1 volume 0.9% sodium chloride to wash the cells and dissolve contaminating salts. Subsequently, the washing solution is removed in a centrifuge running at 5300 g for 20 minutes. The supernatant was discarded and the washed cells collected as pellets. The pellets may be stored by freezing at −20° C. or used directly in the next step.

The pellets comprising the *E. coli* cells were solubilized in about 47 L TRIS buffer used as a binding buffer. After stirring for about one hour 6.4 L detergent (5% LDAO) was added for solubilization to a final concentration of 0.6%. The mixture was incubated overnight at room temperature with gentle stirring. By the resuspension of the cells in a buffer containing a detergent a cell lysis occurred. By the cell lysis membrane proteins are liberated from the internal membranes of the cells and solubilized by the detergent.

To remove negatively charged cell material a polyamine (Superfloc C581) was added in a volume of 427 mL. The mixture was incubated for 30 minutes with stirring at room temperature for coagulating the negatively charged molecules such as cell debris, DNA, RNA and to a certain extent of proteins. The membrane protein solubilized by the detergent remains in the aqueous phase. The mixture is centrifuged at a maximum speed of 5300 g for 15 minutes. The pellet containing the cell debris, DNA, RNA and solubilized proteins are discarded and the supernatant collected. The supernatant is transferred to a container containing 107 L dilution buffer to obtain a final volume of 160 L with a final concentration of 0.2% LDAO.

A column containing the affinity resin "Capto Chelating" from GE healthcare is provided. The resin is charged with Ni2+ which binds to the His10 tag. The column was loaded with the diluted supernatant and subsequently washed with 10 column volumes wash buffer containing 200 mM imidazole to wash out the nonspecific binding components. Subsequently, 2.5 column volumes elution buffer of aqueous 1000 mM imidazole was used to release the membrane protein from the column. The protein eluted from the column was tested by sodium dodecyl sulfate-polyacrylamide gel electrophoresis (SDS-PAGE), which primarily showed a single band indicating a purity of above 80%.

Example 2

An *E. coli* strain BL21 is prepared comprising a vector producing aquaporin proteins linked to a His tag at the C-terminal. The His tag contains ten consecutive histidine molecules attached to the primary sequence of the aquaporin membrane protein.

The *E. coli* strain is nurtured in a standard medium to obtain a total fermentation broth of 250 L. The *E. coli* cells were harvested by filtering the fermentation broth through a PES flat sheet membrane having a pore diameter of 0.05 μm. The filtrate containing the *E. coli* cells is reduced to about 50 L and subsequently subjected to centrifugation at 5300 g in a Sorvall 16 L centrifuge for 20 minutes. Thus, the *E. coli* cells are up-concentrated by microfiltration and the remaining medium is subsequently removed as the supernatant by centrifugation. The pellets may be stored by freezing at −20° C. or used directly in the next step.

The pellets comprising the *E. coli* cells were resuspended in about 50 L buffer (aqueous solution of the protease inhibitor PMSF and EDTA) and homogenized at 1000 bar in a Stansted nm-GEN 7575 homogenizer. To isolate the cell material of interest a polyamine (Superfloc C581) is added in a concentration of 12 ml/L. The temperature was maintained around 10-15° C. The mixture was incubated for 30 minutes with stirring at room temperature. The mixture was centrifuged at a maximum speed of 5300 g for 30 minutes. The pellet contains the membrane protein and the supernatant is discarded.

The pellet was resuspended in a 0.9% sodium chloride solution to obtain a total protein concentration of approximately 50 mg/ml. Solubilization of the membrane protein was performed by adding 28 L TRIS binding buffer and 4.5 liter 5% LDAO to 5 L of the resuspended pellet material. At room temperature and gentle stirring the mixture was allowed to incubate for 2 to 24 hours.

After the solubilization process the mixture was centrifuged in 2 L containers at 5300 g for 90 minutes. The supernatant was recovered and the LDAO concentration was adjusted to 0.2% by addition of dilution buffer.

A column containing the affinity resin "Capto Chelating" from GE healthcare is provided. The resin is charged with Ni$^{2+}$ which binds to the His10 tag. The column was equilibrated by loading binding buffer having 0.2% LDAO. Subsequently, the column was loaded with the diluted supernatant and washed with 10 column volumes wash buffer containing 200 mM imidazole to wash out the nonspecific binding components. Subsequently, 2.5 column volumes elution buffer of aqueous 1000 mM imidazole is used to release the membrane protein from the column. The protein eluted from the column was tested by sodium dodecyl sulfate-polyacrylamide gel electrophoresis (SDS-PAGE) chromatography, which showed only a single band indicating a purity of above 95%.

Example 3

An *E. coli* strain BL21 is prepared comprising a vector producing aquaporin proteins linked to a His tag at the C-terminal. The His tag contains ten consecutive histidine molecules attached to the primary sequence of the aquaporin membrane protein.

The *E. coli* strain is nurtured in a standard medium to obtain a total fermentation broth of 250 L. The fermentation batch had an OD600 13 when harvested, and it was induced for 42.5 hours. The material was homogenized twice at 100 MPa in a Stansted nm-GEN 7575 homogenizer. 10 mL was taken from the lysed material and added to a 15 mL falcon tube.

Centrifugation was then carried out for 1 hour with 5300 g and the pellet was separated from the supernatant. The pellet was then resuspended in 10 mL 0.9% NaCl. BCA assay was used to determine the concentration (mg/mL total protein) of the resuspended pellets and the separated supernatants after the first spin.

The resuspended pellets and the separated supernatants were finally solubilized (1 mL) for 2 hours in 0.6% LDAO (120 uL of 5% LDAO stock from Carbosynth was used to 1 mL material) and were centrifuged again at 5300 G for 15 minutes. Once again, the supernatants were separated from the pellets. The pellets were resuspended (up to 1 mL again) in binding buffer w/o LDAO.

All samples were analyzed on SDS-gel, which showed that around 60% of the proteins in the supernatant was the aquaporin membrane protein.

Example 4

Following the purification of the Aquaporin Z in example 2, the size distribution of the solubilized protein in LDAO was measured.

A comparison was made between the same elution buffer, with and without protein, to evaluate whether the particle size distribution was influenced by the buffer components (including detergent) or the membrane protein.

The Aquaporin Z protein was eluted from the IMAC column using Elution buffer with 1000 mM imidazole and 0.2% w/v LDAO. The purified protein was measured for its protein concentration by amino acid analysis. 6.44 mg/mL of clear, solubilized, protein in Elution buffer was loaded into 3 separate cuvettes (Sarstedt, 4 mL, PMMA, ca. no. 67.755, Numbrecht, Germany) and analyzed for the size distribution by the Malvern Zetasizer Nano-ZS (Malvern Instruments Ltd., Malvern UK) using the Malvern Zetasizer software v.7.02. Results presented in table 1 are the average of the samples run in triplicate.

TABLE 1

| Sample | Concentration of AqpZ (mg/mL) | Size, diameter (d · nm) Population intensity (%) | | |
| --- | --- | --- | --- | --- |
| | | Pop. 1 | Pop. 2 | Pop. 3 |
| Purified AqpZ in Elution buffer (avg.) | 6.44 | 315.6 ± 116.8 nm 45.9% | 108 ± 32.3 nm 35.5% | 17.1 ± 2.5 nm 14.9% |
| Elution buffer (avg.) | 0 | 0.85 ± 0.16 nm 56.8% | 8.6 ± 1.2 nm 41.1% | 103 ± 5.5 nm 2.1% |

The Elution buffer sample (no protein) contains a population distribution with 97.9% of the particles with a size of 8.6 nm or smaller, indicating there are no large detergent micelles in solution that would be retained by microfiltration.

81.4% of the particles in the sample with protein show a size of 108 nm or larger, thereby indicating that the presence of the protein and detergent together form large soluble particles that are retained during microfiltration. The experiment surprisingly shows that large, stable, particles composed of LDAO micelles and membrane protein are produced.

Example 5

Expression of Histidine Tagged Aquaporin from *Oryza sativa Japonica* (Japanese Rice) in *Escherichia coli* and its Purification Using IMAC The gene encoding aquaporin from *Oryza sativa Japonica* (UNIPROT: A3C132) was codon optimized using Geneart's (Subsidiary of Thermo Fischer Scientific) service for improving expression in *E. coli*. The resulting gene was synthesized with the addition of ten histidine encoding codons C-terminally, along with flanking NdeI/XhoI restriction sites N-terminally and C-terminally, respectively (Gene ID: aquaporin_Oryza_sativa_Japonica). The synthetic gene fragment was digested with NdeI/XhoI restriction enzymes and ligated to NdeI/XhoI—digested and purified vector pUP1909 fragment. The resulting ligation mixture was transformed into *Escherichia coli* DH10B and kanamycin resistant transformants were selected on LB agar plates with kanamycin. Transformants were confirmed by sequencing of the genetic construct. Isolated vector DNA was subsequently transferred to the production host, *Escherichia coli* BL21.

In order to heterologously express aquaporin in *E. coli*, the production host was grown in minimal medium consisting of 30 g/L Glycerol, 6 g/L $(NH_4)_2HPO_4$, 3 g/L $KH_2PO_4$, 5 g/L NaCl, 0.25 g/L $MgSO_4·7H_2O$, 0.4 g/L Fe(III)citrate and 1 mL/L sterile filtered trace metal solution. The trace metal solution consisted of 1 g/L EDTA, 0.8 g/L $CoCl_2·6H_2O$, 1.5 $MnC_2·4H_2O$, 0.4 g/L $CuCl_2·2H_2O$, 0.4 g/L $H_3BO_3$, 0.8 g/L $Na_2MoO_4·2H_2O$, 1.3 g/L $Zn(CH_3COO)_2·2H_2O$. After inoculation and overnight growth, additional 0.25 g/L $MgSO_4·7H_2O$ was added.

*E. coli* was cultivated in 3 L Applikon Bioreactors with ez-Control in a batch fermentation process. Protein production was induced by addition of IPTG to a final concentration of 0.5 mM at an optical density (OD 600 nm) of approximately 30. The culture was induced for approximately 24 hours and the bacterial cells were harvested with centrifugation at 5300 g for 20 min.

The pellets comprising the *E. coli* cells were resuspended in buffer (aqueous solution of the protease inhibitor PMSF and EDTA) and homogenized at 1000 bar in a Stansted nm-GEN 7575 homogenizer. The temperature was maintained around 10-15° C. The mixture was centrifuged at a maximum speed of 5300 g for 30 minutes. The pellet contains the membrane protein and the supernatant is discarded.

The pellet was resuspended in a 0.9% sodium chloride solution to obtain a total protein concentration of approximately 50 mg/ml. Solubilization of the membrane protein was performed by adding 28 L TRIS binding buffer and 4.5 liter 5% LDAO to 5 L of the resuspended pellet material. At room temperature and gentle stirring the mixture was allowed to incubate for 2 to 24 hours.

After the solubilization process the mixture was centrifuged in 2 L containers at 5300 g for 90 minutes. The supernatant was recovered and the LDAO concentration was adjusted to 0.2% by addition of dilution buffer.

After solubilization and clarification, the protein was captured using IMAC and eluted in Elution buffer containing 1000 mM imidazole and 0.2% w/v LDAO. The elution fractions were analyzed by SDS Page and only revealed a single major band which migrated at 27 kDa which corresponds to the size of aquaporin from Japanese rice. Furthermore, the result was confirmed by comparison to a negative control purification from *E. coli* transformed with an empty vector. The negative control resulted in no purified protein. Western blot analysis with antibodies (TaKaRa Bio) specific for the histidine-tag resulted as expected in a clear signal from the purified protein and no signal from the negative control confirming the origin of the purified protein as the histidine tagged membrane protein.

Example 6

Expression of Histidine Tagged Aquaporin from *Eucalyptus grandis* in *Escherichia coli* and its Purification Using IMAC The gene encoding aquaporin from *Eucalyptus grandis* (UNIPROT: A0A059C9Z4) was codon optimized using Geneart's (Subsidiary of Thermo Fischer Scientific) service for improving expression in *E. coli*. The resulting gene was synthesized with the addition of ten histidine encoding codons C-terminally, along with flanking NdeI/XhoI restriction sites N-terminally and C-terminally, respectively (Gene ID: aquaporin_*Eucalyptus_grandis*). The gene was cloned and expressed as described in Example 5. The protein was successfully purified and confirmed as described in Example 5.

Example 7

Expression of Histidine Tagged Aquaporin from *Solanum tuberosum* (Danish Potato) in *Escherichia coli* and its Purification Using IMAC The gene encoding aquaporin from *Solanum tuberosum* (UNIPROT: Q38HT6) was codon optimized using Geneart's (Subsidiary of Thermo Fischer Scientific) service for improving expression in *E. coli*. The resulting gene was synthesized with the addition of ten histidine encoding codons C-terminally, along with flanking NdeI/XhoI restriction sites N-terminally and C-terminally, respectively (Gene ID: aquaporin_*Solanum_tuberosum*). The gene was cloned and expressed as described in Example 5. The protein was successfully purified and confirmed as described in Example 5.

Example 8

Expression of Histidine Tagged Aquaporin from *Milnesium tardigradum* (Water Bear) in *Escherichia coli* and Purifying Using IMAC The gene encoding aquaporin from *Milnesium tardigradum* (UNIPROT: G5CTG2) was codon optimized using Geneart's (Subsidiary of Thermo Fischer Scientific) service for improving expression in *E. coli*. The resulting gene was synthesized with the addition of ten histidine encoding codons C-terminally, along with flanking NdeI/XhoI restriction sites N-terminally and C-terminally, respectively (Gene ID: aquaporin_*Milnesium_tardigradum*). The gene was cloned and expressed as described in Example 5. The protein was successfully purified and confirmed as described in Example 5.

Example 9

Expression of Histidine Tagged Aquaporin from *Halomonas* sp. In *Escherichia coli* and its Purification Using IMAC The gene encoding aquaporin from *Halomonas* sp. (UNIPROT: A0A2N0G6U6) was codon optimized using Geneart's (Subsidiary of Thermo Fischer Scientific) service for improving expression in *E. coli*. The resulting gene was synthesized with the addition of ten histidine encoding codons C-terminally, along with flanking NdeI/XhoI restriction sites N-terminally and C-terminally, respectively (Gene ID: aquaporin_*Halomonas*_sp). The gene was cloned and expressed as described in Example 5. The protein was successfully purified and confirmed as described in Example 5.

Example 10

Expression of Histidine Tagged Aquaporin from *Kyrpidia spormannii* in *Escherichia coli* and its Purification Using IMAC The gene encoding aquaporin from *Kyrpidia* sp. (UNIPROT: A0A2K8N5Z5) was codon optimized using Geneart's (Subsidiary of Thermo Fischer Scientific) service for improving expression in *E. coli*. The resulting gene was synthesized with the addition of ten histidine encoding codons C-terminally, along with flanking NdeI/XhoI restriction sites N-terminally and C-terminally, respectively (Gene ID: aquaporin_*Kyrpidia_spormannii*). The gene was cloned and expressed as described in Example 5. The protein was successfully purified and confirmed as described in Example 5.

Example 11

Expression of Histidine Tagged Aquaporin from *Methanothermobacter* sp. In *Escherichia coli* and its Purification Using IMAC The gene encoding aquaporin from *Methanothermobacter* sp. (UNIPROT: A0A223ZCQ2) was codon optimized using Geneart's (Subsidiary of Thermo Fischer Scientific) service for improving expression in *E. coli*. The resulting gene was synthesized with the addition of ten histidine encoding codons C-terminally, along with flanking NdeI/XhoI restriction sites N-terminally and C-terminally, respectively (Gene ID: aquaporin_*Methanothermobacter*_sp). The gene was cloned and expressed as described in Example 5. The protein was successfully purified and confirmed as described in Example 5.

Example 12

Expression of Histidine Tagged Aquaporin from *Novibacillus thermophilus* in *Escherichia coli* and its Purification Using IMAC The gene encoding aquaporin from *Novibacillus thermophilus* (UNIPROT: A0A1U9K5R2) was codon optimized using Geneart's (Subsidiary of Thermo Fischer Scientific) service for improving expression in *E. coli*. The resulting gene was synthesized with the addition of ten histidine encoding codons C-terminally, along with flanking NdeI/XhoI restriction sites N-terminally and C-terminally, respectively (Gene ID: aquaporin_*Novibacillus_thermophilus*). The gene was cloned and expressed as described in Example 5. The protein was successfully purified and confirmed as described in Example 5.

Example 13

Expression of Outer Membrane Protein A (OmpA) from *Escherichia coli* in *E. coli*

Expression and purification of OmpA (UNIPROT: P0A910) in *E. coli* was carried out essentially as described in Example 5, except that *E. coli* was transformed with an empty vector and solubilization was prolonged to 24 hours. The resulting solubilized protein was estimated to a purity of approximately 30-50% by SDS-PAGE, thus clearly stating that OmpA was successfully isolated in the membrane fraction following the standard purification procedure. An additional size exclusion chromatography (SEC) step could have further purified OmpA.

Example 14

Constructing a *Saccharomyces cerevisiae* Strain Expressing Aquaporin-Z (AqpZ) from *Escherichia coli* Fused to an N-Terminal Histidine-Tagged yEGFP and Separated by a Tobacco Etch Virus (TEV) Protease Cleavage Site AqpZ (UNIPROT ID: P60844) from *E. coli* was codon optimized for expression in *S. cerevisiae* using Geneart's service for improved expression in *S. cerevisiae*. For expression in *S. cerevisiae*, AqpZ was fused with yeast enhanced green fluorescent protein (yEGFP) N-terminally (Brendan P. Cormack et al, Microbiology (1997), 143, 303-311) to enable visual detection and quantification of membrane protein expression. Furthermore, eight histidines (His8) was added N-terminally to yEGFP as an IMAC purification tag. The His8-yEGFP and AqpZ was genetically separated by a TEV protease cleavage site incorporated by PCR primers during construction.

Rapid and efficient construction of the plasmid encoding His8-yEGFP-TEV-AqpZ fusion was carried out by in vivo homologous recombination of overlapping regions incorporated by the primers in *S. cerevisiae* between a His8-yEGFP-TEV PCR fragment, a TEV-AqpZ PCR fragment, and the linearized expression plasmid derived from SalI, HindIII and BamHI digestion of the pEMBLyex4 plasmid, as described in (Scientific Reports 7: 16899). The TEV cleavage site enables subsequent removal of the His8-yEGFP protein by the TEV protease.

Selection of *S. cerevisiae* transformants was carried out on minimal medium plates deficient in uracil but supplemented with leucine and lysine to ensure survival of bacterial cells with correctly recombined DNA fragments. Medium composition and amino acid concentrations used in this example were identical to the ones listed in Example 15.

Example 15

Expression of His8-yEGFP-TEV-AqpZ with *Saccharomyces cerevisiae*.

A single colony of transformed yeast cells was selectively propagated until saturation in 5 ml of glucose minimal medium supplemented with 60 mg/L leucine and 30 mg/L lysine. 200 μl of this culture was subsequently propagated in 5 ml of glucose minimal medium supplemented with 30 mg/L lysine for selection for high plasmid copy numbers. Freeze stocks of the high plasmid copy number cells were prepared.

200 μl of a thawed freeze-stock was added to 10 ml of minimal medium supplemented with lysine and grown until saturation. 1 ml of the culture was transferred to 100 ml of the same medium. After overnight growth, an aliquot corresponding to a final OD600 of 0.05 was transferred to 1.5 liters of minimal medium with an initial concentration of 20 g/L glucose as carbon source and 30 g/L glycerol supplemented with extra amino acids. The culture was grown in a 3 L Applikon® bioreactor equipped with ez-Control connected to a PC running Lucullus® software (Applikon, Holland, and SecureCell, Switzerland).

The initial part of the fermentation was performed at 20° C. in minimal medium. The bioreactor was fed with glucose to a final concentration of 3% w/v when the initial amount of glucose had been metabolized. The pH of the growth medium was kept at 6.0 by computer-controlled addition of 1 M $NH_4OH$. When the $CO_2$-exhaust gas leveled off, due to limited access of glucose, the bioreactor was cooled to 15° C. prior to induction of recombinant AQP production. Addition of 50 mL/L expression medium consisting of 400 mL/L ASD-10, 400 mL/L extra amino acids, 200 g/L glycerol and 20 g/L galactose started the expression of the recombinant protein. Yeast cells were harvested after ~96 h.

The minimal medium consisted of 20 g/L glucose, 100 mL/L ASD-10, 5 mL/L V-200, 30 g/L glycerol, 0.1 g/L $Ca_2Cl$. The ASD-10 consisted of 50 g/L $(NH_4)_2SO_4$, 8.75 g/L $KH_2PO_4$, 1.25 g/L $K_2HPO_4$, 5 g/L $MgSO_4 \cdot 7H_2O$, 1 g/L NaCl, 5 mg/L $H_3BO_3$, 1 mg/L KI, 4 mg/L $MnSO_4 \cdot 1H_2O$, 4.2 mg/L $ZnSO_4 \cdot 7H_2O$, 0.4 mg/L $CuSO_4 \cdot 5H_2O$, 2 mg/L $FeCl_3$ and 2 mg/L $Na_2MoO_4 \cdot 2H_2O$. The V-200 consisted of 4 mg/L Biotin, 400 mg/L D-pantothenic acid, 0.4 mg/L Folic acid, 2000 mg/L Myo-inositol, 80 mg/L Niacin, 40 mg/L p-Aminobenzoate, 80 mg/L Pyridoxine, 40 mg/L Riboflavin and 80 mg/L Thiamine. When stated, the medium contained additional amino acids which consisted of 600 mg/L Alanine, 600 mg/L Arginine, 600 mg/L Cysteine, 3000 mg/L Glutamic acid, 2000 mg/L Lysine, 600 mg/L Methionine, 1500 mg/L Phenylalanine, 600 mg/L Proline, 10000 mg/L Serine, 900 mg/L Tyrosine, 4500 mg/L Valine, 2000 mg/L Aspartic acid, 4000 mg/L Threonine, 600 mg/L Histidine and 600 mg/L Tryptophan.

Example 16

Cloning of His8-yEGFP-TEV-AQP5 from *Milnesium tardigradum* in a Bioreactor With *Saccharomyces cerevisiae*

A His8-yEGFP-TEV-AQP5 construct was prepared following the procedure outlined in Example 14. The AQP5 protein from *M. tardigradum* (UNIPROT: G5CTG2) was codon optimized for expression in *E. coli* despite the need for expression in yeast.

Example 17

Purification of His8-yEGFP-TEV-AqpZ and His8-yEGFP-TEV-AQP5 from *S. cerevisiae*

The purification of heterologously expressed membrane protein from *S. cerevisiae* was carried out as described in Example 2, except that applied buffer volumes were scaled down to match the reduced culture volumes and that lysis was carried out at 1800 bar. Protein production and purity was successfully confirmed for both fusion proteins with SDS page and Western Blot and no contaminating proteins could be detected.

The invention claimed is:

1. A pilot or industrial scale process for producing a membrane protein comprising the steps of:
   a. expressing said membrane protein in a host organism present in an aqueous medium,
   b. i) liberating the membrane protein from the host organism by mechanically lysing cells of the host organism to form lysed cell membrane fragments that include the membrane protein and ii) isolating the lysed cell membrane fragments including the membrane protein in the form of a pellet by a first centrifugation,
   c. adding a detergent solution to a resuspension of the pellet obtained in b to solubilize the membrane protein to form a solubilized membrane protein,
   d. recovering a liquid fraction of the solubilized membrane protein obtained in c as a supernatant by a second centrifugation, e. subjecting the liquid fraction to chromatography to bind or retain the solubilized membrane protein on a stationary phase, and f. eluting the protein from the stationary phase to produce the solubilized membrane protein, wherein the first and second centrifugations in steps b and d are each performed at 500 g to 30,000 g and the process does not include ultracentrifugation of the liquid fraction obtained in steps b and d.

2. The process according to claim 1, wherein the aqueous medium comprising the host organism of step a is filtered prior to the liberating of the membrane protein from the host organism according to step b through a microfiltration membrane having a pore diameter of 0.5 micrometer or less.

3. The process according to claim 2, wherein the host organism is isolated after the aqueous medium comprising the host organism is filtered through the microfiltration membrane and by a third centrifugation of the aqueous medium comprising the host organism to form an isolated host organism.

4. The process according to claim 3, wherein the isolated host organism is washed with an isotonic saline solution to dissolve contaminating salts and by a fourth centrifugation of the isotonic saline solution including the isolated host organism to isolate a washed host organism.

5. The process according to claim 1, wherein a dilution buffer is added prior to step b.

6. The process according to claim 1, wherein a cationic flocculant is added to the solubilized membrane protein that is obtained in c to form a suspension.

7. The process according to claim 6, wherein the cationic flocculant is a polyamine compound.

8. The process according to claim 6, wherein the cationic flocculant is allowed to react with cell parts of the suspension during agitation to form flocs, wherein the liquid fraction of step d is recovered as the supernatant from an additional centrifugation of the suspension containing the flocs.

9. The process according to claim 1, wherein the detergent solution added in c is selected from the group consisting of lauryl dimethylamine N-oxide (LDAO), octyl glucoside (OG), dodecyl maltoside (DDM) and combinations thereof.

10. The process according to claim 1, wherein the second centrifugation of step d is performed at 1,000 g to 10,000 g.

11. The process according to claim 1, wherein the membrane protein is associated with a first part of an affinity pair and the stationary phase is associated with a second part of the affinity pair.

12. The process according to claim 11, wherein the first part of the affinity pair is a histidine tag comprising 8 or more histidine molecules.

13. The process according to claim 1, wherein step f includes eluting with an elution buffer which comprises imidazole.

14. The process according to claim 13, wherein the stationary phase capable of binding or retaining the solubilized membrane protein is present in a column and the column prior to elution with the elution buffer, is washed with a washing buffer comprising 40% or less of a concentration of imidazole in the elution buffer.

15. The process according to claim 13, wherein a concentration of imidazole in the elution buffer is 400 mM or more.

16. The process according to claim 1, wherein a cationic flocculant is added to the lysed cell membrane fragments that are obtained in b i) to form a suspension.

17. The process according to claim 6, wherein the cationic flocculant is allowed to react with the lysed cell membrane fragments of the suspension during agitation to form flocs of the lysed cell membrane fragments including the membrane protein and the pellet in b ii) is formed by separating the flocs from the suspension by the first centrifugation.

* * * * *